United States Patent [19]

Dirksing

[11] Patent Number: 5,215,221
[45] Date of Patent: Jun. 1, 1993

[54] DISPOSABLE UNIT DOSE DISPENSER FOR POWDERED MEDICANTS

[75] Inventor: Robert S. Dirksing, Cincinnati, Ohio

[73] Assignee: The Procter & Gamble Company, Cincinnati, Ohio

[21] Appl. No.: 880,146

[22] Filed: May 7, 1992

[51] Int. Cl.$^5$ ............................................. G65D 35/22
[52] U.S. Cl. ..................................... 222/94; 222/633; 406/38; 169/30
[58] Field of Search .......................... 222/94, 541, 633; 169/30, 58; 406/38

[56] References Cited

U.S. PATENT DOCUMENTS

| | | | |
|---|---|---|---|
| 1,377,077 | 5/1921 | Irwin | 222/633 |
| 2,091,081 | 8/1937 | Sharpe | 222/633 |
| 2,331,842 | 10/1943 | Moran | 222/633 |
| 3,637,132 | 1/1972 | Gray | 229/53 |
| 3,964,604 | 6/1976 | Prenntzell | 206/219 |
| 4,238,055 | 12/1980 | Staar | 222/162 |
| 4,301,923 | 11/1981 | Vuorento | 206/484 |
| 4,331,264 | 5/1982 | Staar | 222/94 |
| 4,491,245 | 1/1985 | Jamison | 222/107 |
| 4,717,046 | 1/1988 | Brogli | 222/107 |
| 4,812,067 | 3/1989 | Brown et al. | 401/132 |
| 4,823,985 | 4/1989 | Grollier et al. | 222/1 |
| 4,890,744 | 1/1990 | Lane, Jr. et al. | 206/632 |
| 4,952,068 | 8/1990 | Flint | 366/337 |
| 4,988,016 | 1/1991 | Hawkins et al. | 222/92 |
| 5,018,646 | 5/1991 | Billman et al. | 222/107 |
| 5,048,727 | 9/1991 | Vlasich | 222/209 |
| 5,069,232 | 12/1991 | Staar | 132/320 |

Primary Examiner—Gregory L. Huson
Attorney, Agent, or Firm—Kevin C. Johnson; E. Kelly Linman; Thomas H. O'Flaherty

[57] ABSTRACT

A disposable unit dose dispenser is provided for fluidizing and dispensing a predetermined quantity of powdered product, such as an antihistamine or a decongestant. The dispenser includes a first layer and a second layer connected together to form a gas chamber and a product reservoir adjacent one another. The product reservoir includes a delivery tube adapted to dispense the powdered product. The dispenser also includes a seal which separates the gas chamber from the product reservoir such that when pressure is applied to the gas chamber by squeezing the dispenser the seal ruptures causing a jet of gas to discharge from the gas chamber into the adjacent product reservoir fluidizing and dispensing substantially all of the powdered product from the product reservoir through the delivery tube.

9 Claims, 3 Drawing Sheets

5,215,221

DISPOSABLE UNIT DOSE DISPENSER FOR POWDERED MEDICANTS

BACKGROUND OF THE INVENTION

1. Field of the Invention

The present invention relates to disposable unit dose dispensers, and more particularly, to such disposable unit dose dispensers having a gas chamber and a product reservoir adjacent to the gas chamber for fluidizing and dispensing powdered products, such as medicants, from the dispenser.

2. Description of the Prior Art

The prior art is replete with disposable containers for dispensing both liquid and powdered materials. Many of these containers are of the type which comprise a thermoformed blister and a cover sealed to a flange extending about the periphery of the thermoformed blister. The seal is normally accomplished by fusing the thermoplastic material of the blister and cover or a laminated heat sealable layer in either the blister or cover or both. Packages of this type are often used for single servings of condiments such as in fast food restaurants. The user typically peels the cover from the blister to access the contents.

Another type of prior art disposable container is a disposable blister package which does not require the user to remove the cover to access the product. Instead, the user squeezes the blister causing a predetermined rupture site between the blister and cover to fail in response to pressure within the blister. The rupture site communicates with a second chamber which throttles the emerging product and provides controlled dispensing of the same. While providing improved convenience in dispensing liquid products, packages of the aforementioned type are not well suited to dispense powdered materials which need to be ejected from the dispenser.

SUMMARY OF THE INVENTION

In accordance with one aspect of the present invention a unit dose dispenser is provided for fluidizing and dispensing a predetermined quantity of powdered product. The dispenser has a first flexible layer and a second flexible layer connected together to form a gas chamber and a product reservoir adjacent to the gas chamber. The product reservoir is adapted to store a predetermined quantity of powdered product. The product reservoir includes a delivery tube adapted to dispense the powdered product from the dispenser. The dispenser further includes a seal which separates the gas chamber from the product reservoir such that when pressure is applied to the gas chamber by squeezing the dispenser the seal ruptures causing a jet of gas to discharge from the gas chamber into the adjacent product reservoir fluidizing and dispensing substantially all of the powdered product from the product reservoir through the delivery tube.

In a preferred embodiment the unit dose dispenser includes a weakened seal which separates the gas chamber from the product reservoir and ruptures when pressure is applied to the gas chamber.

In another preferred embodiment the delivery tube includes a break line about which the delivery tube may be opened.

BRIEF DESCRIPTION OF THE DRAWING

While the specification concludes with claims which particularly point out and distinctly claim the invention, it is believed that the present invention will be better understood from the following description of a preferred embodiment(s) taken in conjunction with the accompanying drawings, in which like reference numerals identify identical elements and wherein;

DESCRIPTION OF THE PREFERRED EMBODIMENT

Figure 1:
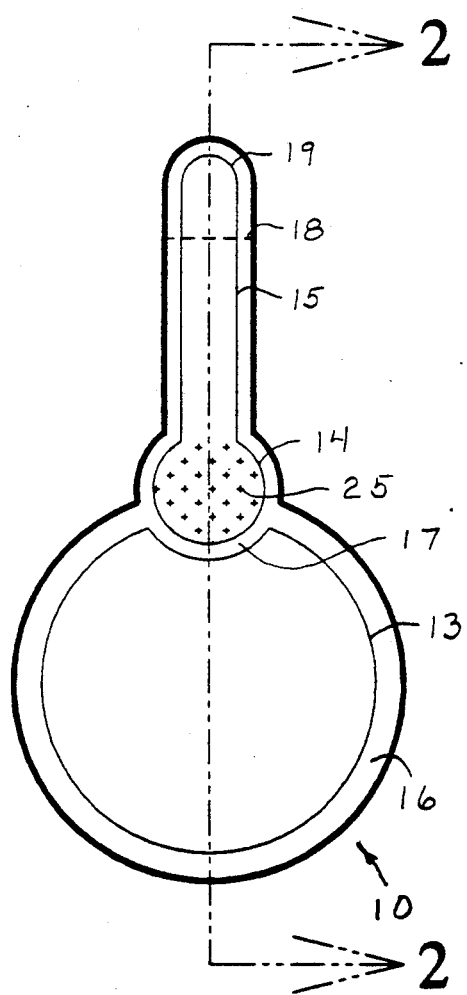
FIG. 1 is a top plan view of a preferred embodiment of a disposable unit dose dispenser of the present invention.
Figure 2:
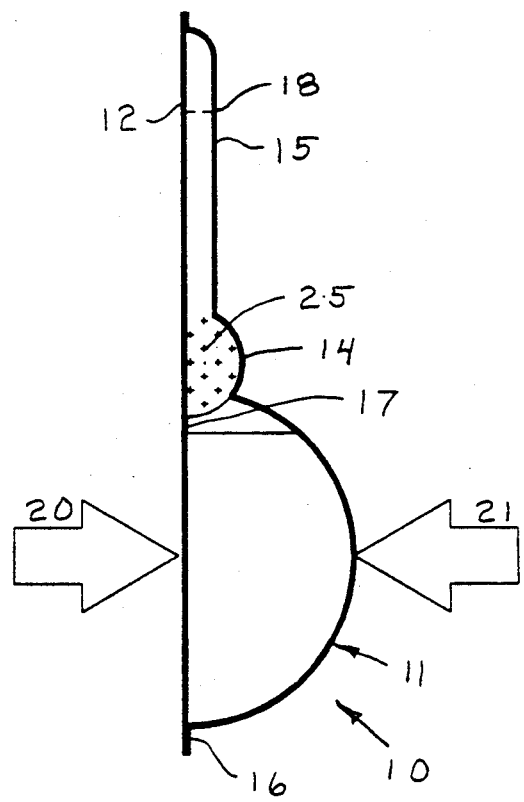
FIG. 2 is a cross-sectional view taken along section line 2—2 of FIG. 1.

In a particular preferred embodiment shown in FIGS. 1 and 2, the present invention provides a disposable unit dose dispenser indicated generally as 10. The disposable unit dose dispenser 10 comprises two main parts, a thermoformed blister 11 and a backsheet 12. As will be appreciated by those skilled in the art, dispenser 10 can be made of a wide variety of materials as well as assume a wide variety of shapes. For example, dispenser 10 may have an oblong, oval, square or rectangular shape, or any combination of shapes. Thermoformed blister 11 is preferably made of a laminated film structure, such as polyethylene terephthalate (PET) and an adhesive layer. Backsheet 12 is preferably made of a similar laminated structure, but having a somewhat thicker and stiffer structure. Of course, other polymeric materials and laminated structures can be used. Special product protection can be maintained by including barrier materials in the laminated structure, such as ethylene-vinyl alcohol (EVOH). It is important when selecting materials for blister 11 and backsheet 12 that they be readably sealable to one another. Furthermore, while backsheet 12 may be relatively stiff, it is important that the material selected for blister 11 be flexible. The thermoformed blister 11 comprises three chambers; a gas or air chamber 13, a product reservoir 14 and a delivery tube 15. A perimeter seal 16 joins chambered blister 11 to backsheet 12 about their respective peripheries. A rupturable seal 17 separates gas chamber 13 from product reservoir 14. Seal 17 follows a portion of the perimeter of product reservoir 14 and intrudes upon the generally spherical shape of gas chamber 13.

Figure 5:
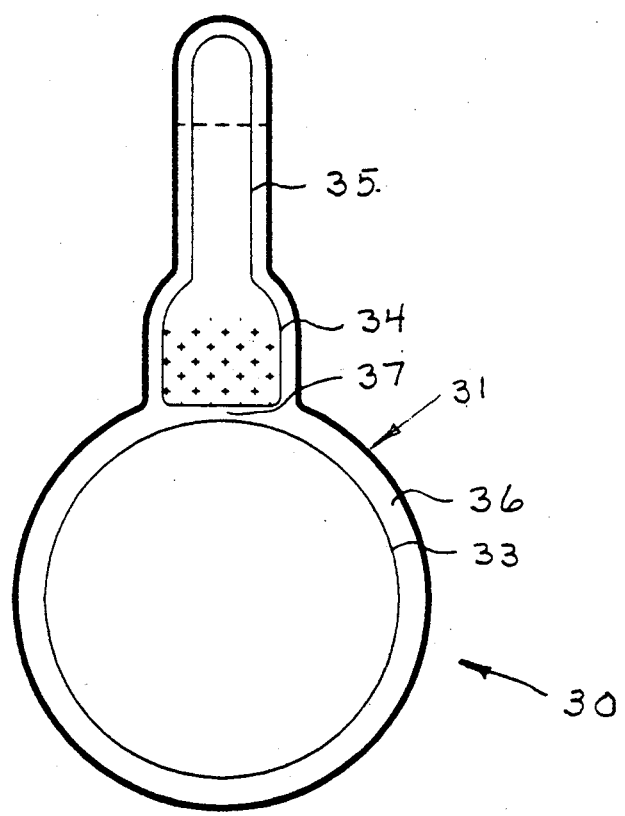
FIG. 5 is a top plan view of another preferred embodiment of a disposable unit dose dispenser of the present invention.

In another preferred embodiment shown in FIG. 5 the disposable unit dose dispenser 30 comprises two main parts, a thermoformed blister 31 and a backsheet 32 (not visible in the plan view). The thermoformed blister comprises three chambers; a gas chamber 33, a product reservoir 34 and a delivery tube 35. A perimeter seal 36 joins the chambered blister 31 to the backsheet 32 about their respective peripheries. A rupturable seal 37 separates gas chamber 33 from the product reservoir 34. Rupturable seal 37 is weakened relative to perimeter seal 36 by reducing the width of seal 37 relative to perimeter seal 36. Other means to preferentially generate rupturing of seal 37 relative to perimeter seal 36 about gas chamber 33, such as reducing the bond strength of the seal, may also be employed.

The unit dose dispenser of the present invention may be manufactured on commercially available equipment generally referred to as "Form, Fill, and Seal". As applied to the unit dose dispenser of the present invention, the various chambers of the dispenser are formed of a sheet of heated thermoplastic, either a single layer of polymer or a laminate. If a break-away tip is desired, the sheet is preferably prescored prior to thermoforming. Next, the product reservoir is filled or partially filled with a predetermined amount of powdered product 25. Subsequently, the backsheet is heat sealed about its periphery to the periphery of the thermoformed blister and at the predetermined rupture site between the gas chamber and product reservoir. Finally, the individual dispensers are cut from the base sheets.

Figures 3, 4:
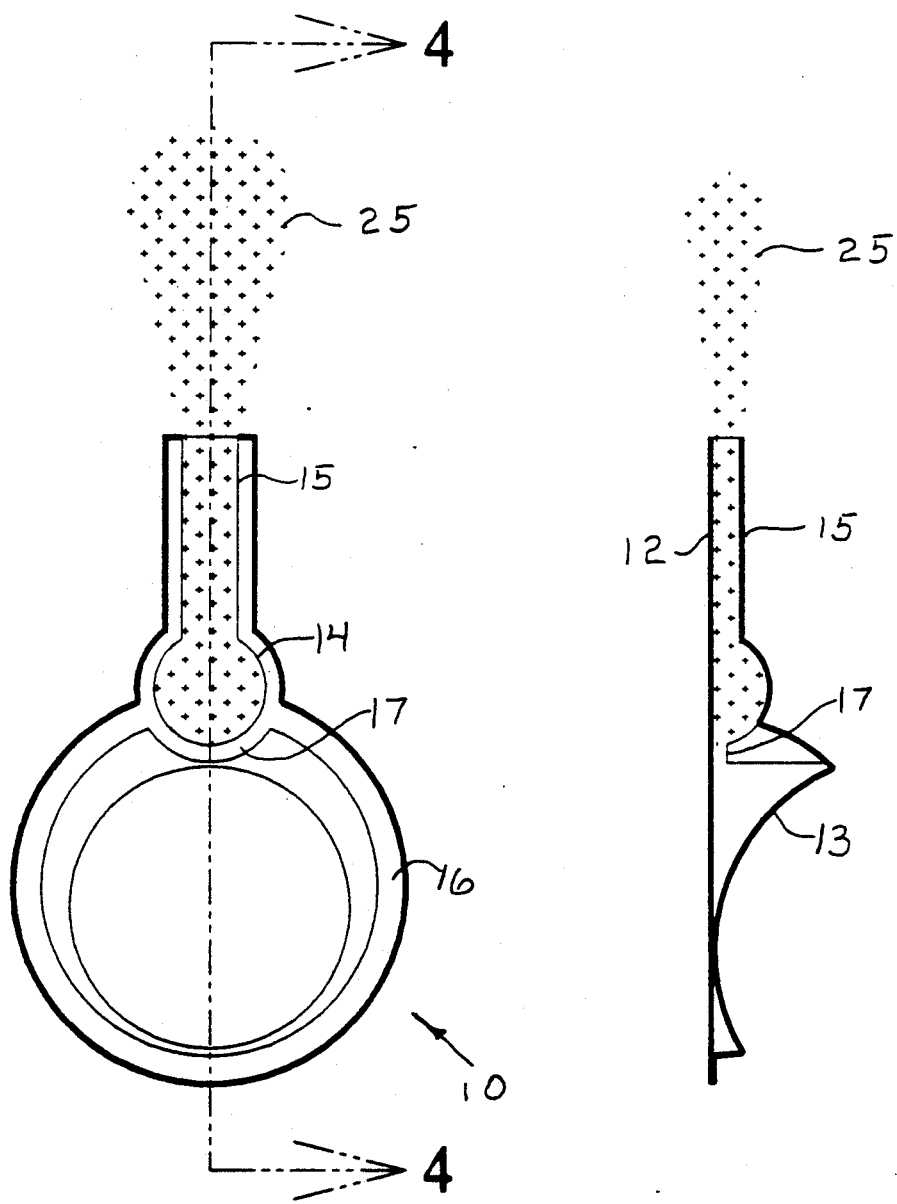
FIG. 3 is a top plan view of the dispenser of the present invention showing the gas chamber in a collapsed condition with the powdered product being ejected from the delivery tube of the dispenser.
FIG. 4 is a cross-sectional view taken along section line 4—4 of FIG. 3.

To use disposable unit dose dispenser 10 the tip 19 of delivery tube 15 is removed along break line 18. Break line 18 is preferably a partially scored line. The scores of break line 18 may be located in thermoformed blister 11 or the adjacent portion of backsheet 12 or both. The tip 19 of delivery tube 15 has been removed from delivery tube 15 in FIGS. 3 and 4. Pressure is applied to gas chamber 13 and its respective adjacent backsheet portion 12 by manually squeezing the dispenser 10, in about the location indicated by arrows 20 and 21, shown in FIG. 2. The increased pressure in gas chamber 13 places stress on perimeter seal 16 and on rupturable seal 17. However, the configuration of seal 17, i.e., the intrusion of seal 17 into the generally spherical gas chamber 13 places increased peeling stress upon seal 17 relative to perimeter seal 16 about gas chamber 13. Seal 17 eventually ruptures and releases the pressurized gas from gas chamber 13 into product reservoir 14 and out through delivery tube 15 as shown in FIGS. 3 and 4. The energy stored in the compressed gas, up to the point of the rupture of seal 17 and the quickness of the collapse of gas chamber 13, causes a jet of air or gas to discharge from gas chamber 13 into the adjacent product reservoir 14. The air jet fluidizes and dispenses powdered product 25 in product reservoir 14 and out through delivery tube 15. Preferably the unit dose dispenser 10 will contain small predetermined doses of medicants which are to be absorbed by the body through the nasal cavity. Examples of such medicants include antihistamines, decongestants, asthma, and allergy medications.

While particular embodiments of the present invention have been illustrated and described, it will be obvious to those skilled in the art that various changes and modifications may ge made without departing from the spirit and scope of the invention, and it is intended to cover in the appended claims all such modifications that are within the scope of this invention.

What I claim is:

1. A unit dose dispenser for fluidizing and dispensing a predetermined quantity of powdered product, said dispenser comprising a first layer and a second layer connected together to form a gas chamber and a product reservoir adjacent said gas chamber for storing said predetermined quantity of powdered product, said product reservoir including a delivery tube adapted to dispense said powdered product from said dispenser, said dispenser further including a frangible seal which separates said gas chamber from said product reservoir preventing gas in said gas chamber from mixing with said predetermined quantity of powdered product in said product reservoir prior to rupturing of said frangible seal, such that when pressure is applied to said gas chamber by squeezing said dispenser said frangible seal ruptures causing a jet of gas to discharge from said gas chamber into said adjacent product reservoir fluidizing and dispensing substantially all of said powdered product from said product reservoir through said delivery tube.

2. A unit dose dispenser according to claim 1, wherein said first flexible layer is a laminated structure comprising of at least one polymeric layer and a heat sealable adhesive layer.

3. A unit dose dispenser according to claim 1, wherein said second flexible layer is a laminated structure comprising of at least one polymeric layer and a heat sealable adhesive layer.

4. A unit dose dispenser according to claim 1, wherein said delivery tube includes a break line about which said delivery tube may be opened.

5. A unit dose dispenser according to claim 1, wherein said seal separating said gas chamber from said product reservoir includes a weakened portion to permit rupture thereof in response to squeezing forces applied to said dispenser.

6. A unit dose dispenser for fluidizing and dispensing a predetermined quantity of powdered product, said dispenser comprising a first flexible layer and a second flexible layer connected together to form a gas chamber and a product reservoir adjacent said gas chamber for storing said predetermined quantity of powdered product, said product reservoir including a delivery tube adapted to dispense said powdered product from said dispenser, said dispenser further including a frangible seal having a weakened portion, said frangible seal separating said gas chamber from said product reservoir preventing gas in said gas chamber from mixing with said predetermined quantity of powdered product in said product reservoir prior to rupturing of said frangible seal, such that when pressure is applied to said gas chamber by squeezing said dispenser, said weakened portion in said frangible seal ruptures causing a jet of gas to discharge from said gas chamber into said adjacent product reservoir fluidizing and dispensing substantially all of said powdered product from said product reservoir through said delivery tube.

7. A unit dose dispenser according to claim 6, wherein said first flexible layer is a laminated structure comprising of at least one polymeric layer and a heat sealable adhesive layer.

8. A unit dose dispenser according to claim 6, wherein said second flexible layer is a laminated structure comprising at least one polymeric layer and a heat sealable adhesive layer.

9. A unit dose dispenser according to claim 6, wherein said delivery tube includes a break line about which said delivery tube may be opened.

* * * * *